United States Patent [19]

Smith et al.

[11] Patent Number: 5,358,935

[45] Date of Patent: Oct. 25, 1994

[54] NONANTIGENIC KERATINOUS PROTEIN MATERIAL

[75] Inventors: Robert A. Smith, 2246 E. Northside Dr., Jackson, Miss. 39211; Cheryl R. Blanchard; James Lankford, Jr., both of San Antonio, Tex.

[73] Assignee: Robert Allen Smith, Jackson, Miss.

[21] Appl. No.: 978,768

[22] Filed: Nov. 19, 1992

[51] Int. Cl.$^5$ .................. A61F 2/02; A61K 37/12; C07K 3/02
[52] U.S. Cl. ......................... 514/21; 424/422; 424/423; 514/937; 530/357; 530/427; 530/842; 623/11; 623/901
[58] Field of Search .......... 530/357, 402, 427, 842; 514/21, 937; 424/422, 423; 252/308, 311; 623/8, 11, 15, 901

[56] References Cited

U.S. PATENT DOCUMENTS

| | | | |
|---|---|---|---|
| 1,214,299 | 1/1917 | Grosvenor et al. | 530/357 |
| 3,699,969 | 10/1972 | Allen | 623/15 |
| 4,021,522 | 5/1977 | Daniel | 530/356 |
| 4,140,537 | 2/1979 | Luck et al. | 530/356 |
| 4,233,360 | 11/1980 | Luck et al. | 428/310 |
| 4,250,139 | 2/1981 | Luck et al. | 422/21 |
| 4,424,208 | 1/1984 | Wallace et al. | 514/21 |
| 4,481,001 | 11/1984 | Graham et al. | 434/267 |
| 4,557,764 | 12/1985 | Chu | 106/161 |
| 4,582,640 | 4/1986 | Smestad et al. | 514/801 |
| 4,642,117 | 2/1987 | Nguyen et al. | 623/11 |
| 4,655,980 | 4/1987 | Chu | 530/356 |
| 4,725,671 | 2/1988 | Chu et al. | 530/356 |
| 4,795,467 | 1/1989 | Piez et al. | 623/16 |
| 4,803,075 | 2/1989 | Wallace et al. | 424/423 |
| 4,865,602 | 11/1989 | Smestad et al. | 623/16 |
| 4,950,483 | 8/1990 | Ksander et al. | 424/422 |
| 4,959,213 | 9/1990 | Brod et al. | 514/21 |
| 5,035,715 | 7/1991 | Smestad et al. | 623/16 |
| 5,108,436 | 4/1992 | Chu et al. | 623/66 |

FOREIGN PATENT DOCUMENTS

| | | |
|---|---|---|
| 89152 | 9/1983 | European Pat. Off. |
| 250264 | 10/1989 | Japan . |
| 590955 | 8/1947 | United Kingdom ............. 530/357 |

OTHER PUBLICATIONS

Am. J. Ontology, vol. 11, issued Jan. 1990, Huang et al, "A Morphometric Study of the Effects of Pressure . . . ", pp. 39–43.

Joussen, K. "Initial Experiences with Collagen . . . ", vol. 35 No. 7, pp. 291–295 (translation not available).

Wallace, et al., "Injectable cross-linked collagen with improved flow properties", *Journal of Biomedical Materials Research*, vol. 23, 931–945 (1989).

(List continued on next page.)

Primary Examiner—Jeffrey E. Russel
Attorney, Agent, or Firm—Vaden, Eickenroht, Thompson, Boulware & Feather

[57] ABSTRACT

The present invention is a new nonantigenic keratinous protein material that may be used as a number of purposes, including correction of soft tissue deficiencies and the creation of biomedical implants and implant coatings. The present invention also includes processes for using the nonantigenic keratinous protein material for soft tissue augmentation, creating implants, and the coating of biocompatible implants. The nonantigenic keratinous protein material can be formed by obtaining nonantigenic keratinous protein and processing it to a powder form. If hair from the recipient or a compatible doner is used, it is bleached and rinsed, then dried and chopped into about 0.25 inch pieces. The keratinous protein is then homogenized in a solvent to a particular size generally in the range of about 0.1 to about 500 μm. The particles are then ultrasonicated in a solvent. Afterwards, the solvent is evaporated, and the powdered protein is sterilized and suspended in a sterile bioinert solvent to create a protein colloid at a solids concentrations suitable for injection.

12 Claims, No Drawings

OTHER PUBLICATIONS

Skorman, Steven E., "Use of Injectable Collagen to Treat Chronic Diabetic Foot Ulcers", *The Journal of Foot Surgery*, vol. 26, 511–515 (1987).

McPherson, John M., et al., "The Influence of Heparin on the Wound Healing Response to Collagen Implants in vivo", *Collagen Rel. Res.*, vol. 1, 83–100 (1988).

McPherson, John M., et al., "The Effects of Heparin on the Physicochemical Properties of Reconstituted Collagen", *Collagen Rel. Res.*, vol. 1, 65–82 (1988).

DeLustro, Frank, Ph.D., et al. "Immune Responses to Allogeneic and Xenogeneic Implants of Collagen and Collagen Derivatives", *Clinical Orthopaedics and Related Research*, Section III: Basic Science and Pathology, vol. 260, 263–279 (Nov. 1990).

Cahill, Kenneth V., M.D., and John A. Burns, M.D., "Volume Augmentation of the Anophthalmic Orbit With Cross-linked Collagen (Zyplast)", *Arch Ophthalmol*, vol. 107, 1684–1687 (Nov. 1989).

Symmers, W. St. C., Sen. M.D., "Silicon Mastitis in 'Topless' Waitresses and Some Other Varieties of Foreign-body Mastitis", *Br. med. J.* vol. 3, 19–22 (1968).

Trentham, David E., M.D., "Adverse Reactions to Bovine Collagen Implants: Additional Evidence for Immune Response Gene Control of Collagen Reactivity in Humans", *Arch Dermatol*, vol. 122, 643–644 (Jun. 1986).

Ersek, Robert A., M.D., F.A.C.S. and Arthur A. Beisand, III, M.D., "Bioplastique TM: A New Biphasic Polymer for Minimally Invasive Injection Implantation", *Aesth. Plast. Surg.*, vol. 16, 59–65 (1992).

Prime, Frederick, Jr., M.D., "The Prevention of Postoperative Adhesions Between the Cortex and Dura", *Univ. Penn. Med. Bull.*, vol. 22, 57–61 (1909).

Chao, Yi-Cheng, M.D., Storer Humphreys, M.D., and Wilder Penfield, M.D., D.Sc., "A New Method of Preventing Adhesions: The Use of Amnioplastin After Craniotomy", *Br. med. J.*, vol. 1, 517–519 (1940).

Moscona, R., M.D., et al., "Free-Fat Injections for the Correction of Hemifacial Atrophy", *Plast. Reconstr. Surg.*, vol. 84(3), 501–507 (1989).

"Collagen Wins Court Case Filed by Woman Claiming Treatments Are Defective", *Collagen Corporation News Release*, UPI, Oct. 16, 1991.

Spira, Melvin, M.D., and Theodore Rosen, MD, "Injectable Soft Tissue Substitutes", *Derm. for Plast. Surg.*, vol. 20(1), 181–188 (1993).

NONANTIGENIC KERATINOUS PROTEIN MATERIAL

TECHNICAL FIELD

The present invention is a new nonantigenic keratinous protein material that may be used for a number of purposes, including the correction of soft tissue deficiencies and the creation of biomedical implants and implant coatings. The present invention also includes processes for using the nonantigenic keratinous protein material for soft tissue augmentation, creating implants, and the coating of biocompatible implants.

BACKGROUND OF THE INVENTION

A strong demand exists among medical specialists for a nonantigenic, nonmigratory, biocompatible filler material for correcting soft tissue deficiencies. Historically, the correction of contour deficiencies with various filler materials has met with failure or limited success. Early injectable filler materials included oils, mica, and autologous fat. Prime F., "The Prevention of Postoperative Adhesions Between the Cortex and Dura", *Univ. Penn. Med. Bull.*, 20: 57-61 (1909); Chao, Y., et al., "A New Method of Preventing Adhesions: The Use of Amniplastin After Craniotomy", *Br. Med. J.*, 1: 517-19 (1940); Muscona, R., "Free Fat Injections for The Correction of Hemifacial Atrophy", *Plast. Reconstr. Surg.*, 85(3):501 (1989). Synthetic biocompatible filler materials such as silicone fluid and Teflon ® have also met with limited success. Both of those materials migrate from the injection site to other parts of the body with deleterious results. Symmers, W., "Silicone Mastitis In "Topless" Waitresses And Some Varieties of Foreign Body Mastitis", *Br. Med. J.*, 3: 19 (1968)

Presently, bovine dermal collagen is the most widely used filler material and is used in the form of an injectable protein. Unfortunately, it is antigenic and therefore is attacked by the body's immune system. The foreign collagen is broken down so that periodic replacement treatments are required. Trenthan, D. E, "Adverse Reactions To Bovine Collagen Implants," *Arch. Dermatol.*, 122: 643-44 (1986). Patients treated with bovine dermal collagen have complained of adverse results ranging from allergic responses to rare autoimmune diseases. Press Release, "Collagen Wins—Court Case Filed By Woman claiming Treatments Are Defective", United Press International, Oct. 16, 1991.

Recently, a new synthetic polymer called Bioplastique ® has been introduced to the market for permanent soft tissue augmentation through injection. Unfortunately, Bioplastique ® is largely ineffective since it cannot be injected into the dermis, but must be injected subdermally. This is due to the fact that Bioplastique ® consists of 100 to 400 µm particles of dimethylsiloxame suspended in a biodegradable hydrogel. These particles are too large to enter the dermis. Ersek, R. A., "Bioplastique ®: A New Biphasic Polymer For Minimally Invasive Injection Implantation", *Aesth, Plast. Surg.*, 16: 59-65 (1992).

A strong need also exists for biomedical implants and implant coatings that are biocompatible, nontoxic, and structurally and chemically stable. Such implants and coatings would replace bone and cartilage in applications ranging from maxillofacial reconstruction to total joint replacement.

The present invention is a new nonantigenic keratinous protein material that is derived from a compatible donor, or from the potential recipient of the material. Consequently, the material does not invoke a deleterious immunological reaction in a recipient, thus meeting a long-standing need for both filler material for correcting soft tissue deficiencies and for an implant material. More specifically, keratinous protein is advantageous as used in the present invention because it does not autobiodegrade due to either the enzymatic systems or the immune system of the body, thus making it permanent for the life of the patient and nonantigenic. Furthermore, the protein particles of this invention are small enough for injection into the dermis.

SUMMARY OF THE INVENTION

A new nonantigenic keratinous protein material has been developed that may be used for a number of purposes, including the correction of soft tissue deficiencies and the creation of biomedical implants and implant coatings. The nonantigenic keratinous protein material is derived from a compatible donor or from the potential recipient of the material, so it does not invoke a deleterious immunological reaction in a recipient. The material is nonmigratory, bioinert, and permanent.

When this material is in a protein colloid form with a low solids concentration, it can be injected into the soft tissue of a recipient. The injectable colloid embodiment of the present invention comprises a suspension of powdered nonantigenic keratinous protein in a sterilized bioinert solvent at a solids concentration suitable for injection. The nonantigenic keratinous protein can be prepared from hair or nails of the recipient or a compatible donor. The solids concentration of the powdered keratinous protein is preferably in the range of 30 to 70 percent by volume of the protein colloid.

The nonantigenic protein of the present invention in a solid form is also advantageous as an implant material for numerous medical applications, including replacement of bone or cartilage. Such implants may be made entirely of the nonantigenic keratinous protein or may be mixed with a biocompatible material to form a composite. Alternatively, the nonantigenic keratinous protein may be coated onto the surface of a biocompatible implant material to provide a nonantigenic interface between an implant recipient's tissue and the biocompatible material. The biocompatible implant material may be high density polyethylene ("HDPE"), silicone, Teflon ®, aluminum oxide, zirconium oxide, hydroxyapatite or other biocompatible materials.

A process for soft tissue augmentation has been developed using the nonantigenic protein colloid. The process involves obtaining nonantigenic keratinous protein and processing it to a powder form. If hair from the recipient or a compatible donor is used, it is bleached and rinsed, then dried and chopped into about 0.25 inch pieces. The keratinous protein is then homogenized in a solvent to a particle size generally in the range of about 0.1 to about 500 µm. The particles are then ultrasonicated in a solvent. Afterwards, the solvent is evaporated, and the powdered protein is sterilized and suspended in a sterile bioinert solvent to create a protein colloid at a solids concentration suitable for injection. The process is completed by loading an injection apparatus with the protein colloid and injecting the protein colloid into a soft tissue area of a recipient.

The present invention also includes a process for implantation using the nonantigenic keratinous protein material. This process comprises the steps of processing the nonantigenic keratinous protein to a preselected particle size; fabricating a solid implant made entirely of nonantigenic keratinous protein or mixed with a biocompatible material to form a composite; and inserting the implant into a recipient.

A process for using the nonantigenic keratinous protein material as a coating for biocompatible implants is also part of the present invention. The process comprises the steps of processing the nonantigenic keratinous protein to a preselected particle size; coating the surface of a biocompatible implant; and inserting the implant into a recipient.

DESCRIPTION OF THE PREFERRED INVENTION

The new nonantigenic keratinous protein material may be harvested from a potential recipient of the material or from a compatible donor. Once the protein material is obtained, it may be used as an injectable colloid, a solid implant, or as an implant coating.

The preferred embodiment of the present invention comprises a nonantigenic keratinous protein colloid that can be used for numerous applications, depending upon the protein particle size and solids concentration of the prepared colloid. In a colloidal suspension the protein is suitable for injection for soft tissue augmentation. In addition, the powdered protein can be formed into an implant or used as an implant coating.

In one preferred embodiment of the invention, the nonantigenic protein colloid comprises a suspension of the powdered nonantigenic keratinous protein in a sterilized bioinert solvent at a solids concentration of 30 to 70% by volume, which is a suitable concentration for injection. The keratinous protein may be obtained from any nonantigenic source. In the preferred embodiment, however, the source of keratinous protein is hair from the intended recipient. Examples of suitable bioinert solvents used for suspension of the protein include saline and peanut oil. The protein is processed to powder form by the process described below.

Another preferred embodiment of the present invention is a nonantigenic keratinous protein which is suitable for an implant or an implant coating. When an implant is formed entirely of the nonantigenic protein colloid, it is formed through the process described below. When the implant is a composite of the keratinous protein and a biocompatible material, it can be a mixture of the protein colloid and a biocompatible material, or it can have an inner core of the biocompatible material and a coating of the keratinous protein. Such implants are created by the processes described below.

In the preferred process of the present invention, the nonantigenic keratinous protein material is harvested from the hair or nails of the potential recipient or a compatible donor. In one preferred method, the keratinous protein is harvested from the hair of a recipient. For processing a batch of five grams ("g") of hair, it was first bleached with a commercially available hair bleach kit. Thereafter, the bleach solution is washed from the hair with a soap solution such as Alconox ®, followed by thoroughly rinsing with deionized water.

Next, the hair is strained from the washing solutions and dried typically in an oven preferably for about 1.5 hours at 75° C. The dried hair is then manually cut to a free flowing size of about one-fourth inch. The chopped hair is suspended in a cooled solvent such as acetone. Cooling of the solvent is accomplished with an ice bath or with other suitable means. The chopped hair is then homogenized. Preferably, the hair is homogenized for 2 hours at high speed with an OMNI 5000 homogenizer (Omni, Int'l.). This mechanically reduces bleached hair through a shearing process to particles and whiskers generally in the range of about 0.1 to 500 $\mu$m. While the particle sizes range typically from about 0.1 to 500 $\mu$m, it is possible to segregate the hair particles according to their size. Prior to sterilization, the particles are subjected to standard methods of filtration or sedimentation to obtain a particle size that is suitable for the specific intended use of that keratinous protein.

Sonication is performed next on the homogenized hair. During this procedure, the hair is also maintained in cooled acetone. The hair is sonicated for about 15 minutes in a Heat Systems—Ultrasonics, Inc. Sonic Bath. This disperses and deagglomerates the hair particles and whiskers.

Thereafter, the acetone is evaporated from the hair in an oven for approximately 4 hours at 75° C. A powder-like hair substance results. This dry protein residue is sterilized by standard steam or gas autoclaving techniques and subsequently suspended in a sterile carrier. The carrier may be saline, peanut oil, or any other bioinert solvent to create a protein colloid with a solids concentration in the range of 30 to 70 percent by volume. The solids content of the colloid may be varied to suit a range of applications. A denser colloid may be more desirable for certain procedures. The amount of dried protein added to carrier is adjusted accordingly.

Following resuspension of the keratinous protein, the protein colloid is loaded into an injection apparatus and injected into a soft tissue area of a recipient.

Alternatively, the powdered nonantigenic keratinous protein is fabricated into a solid implant. Fabrication is accomplished by pressing the hair powder into the desired shape and heating to effectively fuse the hair into a solid monolithic mass of protein. This can be done through standard methods using a steam autoclave. The hair particles are bonded together as described above, in the form of an implant, so that the implant is ready for insertion into the recipient. Thereafter implantation is performed.

In another preferred process for implantation, the keratinous protein is subjected to the same treatment as described immediately above for implantation, except that the protein colloid is mixed into or coated onto a biocompatible material to create a nonantigenic composite implant. The keratinous protein in or on the composite implant provides a nonantigenic interface between the implant recipient's tissue and the biocompatible material. The biocompatible material used in the implant is selected from a group consisting of high density polyethylene ("HDPE"), silicone, Teflon ®, aluminum oxide, zirconium oxide, hydroxyapatite, or other biocompatible materials. The composite implant is formed by mixing 5–60 vol % of powdered protein homogeneously with a polymer suitable for implantation and solidifying through cooling. Alternatively, the coated implant is formed by spraying or dipping a pre-existing biocompatible material with the protein powder suspended in a fugitive solvent, such as acetone. The coating would then be bonded together by heating this forming a coherent nonantigenic protein coating.

While the preferred processes of the invention stated above use hair as the source of nonantigenic keratinous protein, any source of nonantigenic keratinous protein may be used. For sources of keratinous protein other than hair, the processes for fabricating the injectable colloid, implants, and implant coatings remain substantially the same.

We claim:

1. A nonantigenic implant material comprising:
   (a) a nonantigenic keratinous protein processed to a powder form;
   (b) a biocompatible material combined with the processed keratinous protein to provide a nonantigenic interface between an implant recipient's tissue and the biocompatible material; and
   (c) said processed keratinous material is coated onto the surface of the biocompatible material.

2. The nonantigenic implant material according to claim 1 in which the biocompatible material is selected from the group consisting of HDPE, silicone, Teflon ®, aluminum oxide, zirconium oxide, and hydroxyapatite.

3. A process for preparing a nonantigenic protein colloid for soft tissue augmentation comprising the steps of:
   (a) processing a nonantigenic keratinous protein from a compatible donor to a powder form;
   (b) suspending the powdered protein in a sterilized bioinert carrier to create a protein colloid at a solids concentration in the range of 30 to 70 percent by volume that is suitable for injection; and
   (c) injecting the protein colloid into a recipient.

4. The process of claim 3 wherein the compatible donor in step (a) is also the recipient of the protein colloid.

5. A process of claim 3 wherein the keratinous protein in step
   (a) is selected from the group consisting of hair and nails.

6. A process for soft tissue augmentation using the process for preparing a nonantigenic protein colloid of claim 3 comprising the additional steps of:
   (a) loading an injection apparatus with the protein colloid; and
   (b) injecting the protein colloid into a soft tissue area of a recipient.

7. (Amended) A process for preparing a nonantigenic protein colloid for soft tissue augmentation comprising the steps of:
   (a) bleaching hair obtained from a compatible donor;
   (b) rinsing the bleached hair in a soap solution and deionized water to remove the bleaching agent;
   (c) drying the rinsed hair for about 1.5 hours at about 75° C.;
   (d) chopping the dried hair to about 0.25 inch pieces;
   (e) homogenizing the chopped hair in a cooled solvent to a particle size in the range of about 0.1 $\mu$m to about 500 $\mu$m;
   (f) sonicating the homogenized hair in a cooled solvent;
   (g) evaporating the solvent to leave a powdered hair residue;
   (h) sterilizing the powdered hair residue; and
   (i) suspending the sterilized powdered hair residue in a sterilized bioinert carrier to create a colloid with a solids concentration in the range of 30 to 70 percent by volume.

8. A nonantigenic protein colloid produced by the process of claim 7.

9. A process for soft tissue augmentation using the process for preparing a nonantigenic protein colloid of claim 3 comprising the additional steps of:
   (a) loading an injection apparatus with the protein colloid; and
   (b) injecting the protein colloid into a soft tissue area of a recipient.

10. A process for preparing and implanting a nonantigenic implant comprising the steps of:
    (a) processing a compatible nonantigenic keratinous protein to a powder form;
    (b) coating the powder form keratinous protein onto the surface of a biocompatible implant material; and
    (c) implanting said keratinous powder coated nonantigenic composite implant into a recipient.

11. A process of claim 10 wherein the biocompatible material of step (b) is selected from the group consisting of HDPE, silicone, Teflon ®, aluminum oxide, zirconium oxide, and hydroxyapatite.

12. A process for preparing a nonantigenic implant comprising the steps of:
    (a) processing a nonantigenic keratinous protein to a powder form; and
    (b) bonding the nonantigenic keratinous protein powder prepared in step (a) by pressure treatment into the form of a solid monolithic implant.

* * * * *